(12) United States Patent
Blücher

(10) Patent No.: US 9,127,189 B2
(45) Date of Patent: Sep. 8, 2015

(54) COATING FOR OBJECTS, IN PARTICULAR IN PUBLIC FACILITIES AND/OR MEANS OF TRANSPORTATION, FOR PREVENTING THE TRANSMISSION OF INFECTIONS

(75) Inventor: Hasso von Blücher, Erkath (DE)

(73) Assignee: Blucher Gmbh, Erkrath (DE)

( * ) Notice: Subject to any disclaimer, the term of this patent is extended or adjusted under 35 U.S.C. 154(b) by 123 days.

(21) Appl. No.: 13/503,541

(22) PCT Filed: Aug. 27, 2010

(86) PCT No.: PCT/EP2010/005256
§ 371 (c)(1),
(2), (4) Date: Jul. 3, 2012

(87) PCT Pub. No.: WO2011/047747
PCT Pub. Date: Apr. 28, 2011

(65) Prior Publication Data
US 2012/0261054 A1    Oct. 18, 2012

(30) Foreign Application Priority Data

Oct. 22, 2009  (DE) .......................... 10 2009 050 425

(51) Int. Cl.
| | |
|---|---|
| *A61K 9/00* | (2006.01) |
| *C09J 7/02* | (2006.01) |
| *A01N 25/34* | (2006.01) |
| *E05B 1/00* | (2006.01) |
| *C08K 3/00* | (2006.01) |
| *C08K 3/08* | (2006.01) |

(52) U.S. Cl.
CPC ............... *C09J 7/0264* (2013.01); *A01N 25/34* (2013.01); *C09J 7/0296* (2013.01); *E05B 1/0069* (2013.01); *C08K 3/005* (2013.01); *C08K 3/08* (2013.01); *C09J 2205/106* (2013.01)

(58) Field of Classification Search
None
See application file for complete search history.

(56) References Cited

U.S. PATENT DOCUMENTS

| | | | | |
|---|---|---|---|---|
| 3,737,723 | A * | 6/1973 | Kanor ........................... | 361/223 |
| 5,069,907 | A * | 12/1991 | Mixon et al. ................... | 424/445 |
| 5,882,667 | A * | 3/1999 | Jones ............................. | 424/405 |
| 2004/0039343 | A1* | 2/2004 | Eppstein et al. .............. | 604/200 |
| 2004/0072002 | A1* | 4/2004 | Hashioka et al. ............. | 428/515 |
| 2005/0249791 | A1* | 11/2005 | Hobbs et al. .................. | 424/443 |
| 2006/0010652 | A1* | 1/2006 | Kellaher et al. ................ | 16/413 |
| 2006/0078484 | A1* | 4/2006 | Greep ........................... | 422/300 |
| 2007/0031546 | A1* | 2/2007 | Nelson et al. ................. | 426/106 |
| 2009/0130157 | A1* | 5/2009 | Ylitalo et al. .................. | 424/405 |
| 2009/0155328 | A1* | 6/2009 | Lee ............................... | 424/405 |
| 2011/0070418 | A1* | 3/2011 | Ellingson et al. ............. | 428/218 |

* cited by examiner

*Primary Examiner* — Robert A Wax
*Assistant Examiner* — Olga V Tcherkasskaya
(74) *Attorney, Agent, or Firm* — Edward E. Sowers; Brannon Sowers and Cracraft PC

(57) ABSTRACT

The invention relates to a covering (1) for objects, in particular in public facilities and/or means of transportation, for preventing the transmission of infections, the covering being made of covering material, in particular having a virucidal and/or virostatic and/or bactericidal and/or bacteriostatic and/or fungicidal and/or fungistatic effect, wherein the covering material is intended to be applied externally to surfaces (2) of objects. According to the invention, the covering material is flexible and can be adapted to the outer shape of the object.

8 Claims, 5 Drawing Sheets

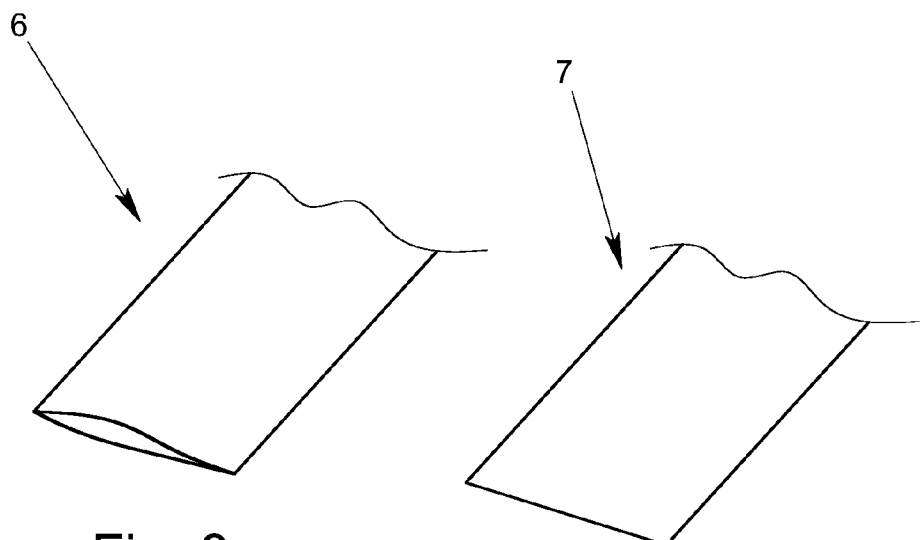
Fig. 8
Fig. 9
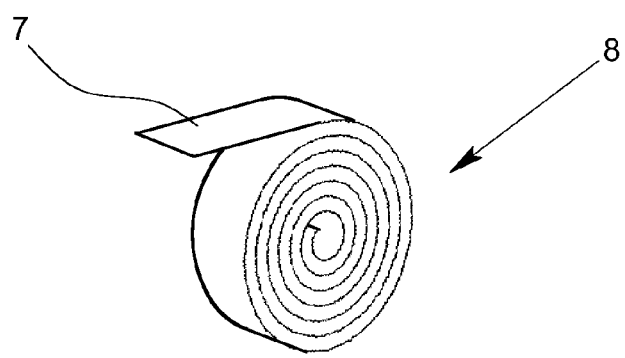
Fig. 10

COATING FOR OBJECTS, IN PARTICULAR IN PUBLIC FACILITIES AND/OR MEANS OF TRANSPORTATION, FOR PREVENTING THE TRANSMISSION OF INFECTIONS

CROSS-REFERENCES TO RELATED APPLICATIONS

This application is a National Stage filing of International Application PCT/EP 2010/005256, filed Aug. 27, 2010, entitled "COATING FOR OBJECTS, IN PARTICULAR IN PUBLIC FACILITIES AND/OR MEANS OF TRANSPORTATION, FOR PREVENTING THE TRANSMISSION OF INFECTIONS" claiming priority to German Application No. DE 10 2009 050 425.7 filed Oct. 22, 2009. The subject application claims priority to PCT/EP 2010/005256, and to German Application No. DE 10 2009 050 425.7 and incorporates all by reference herein, in their entirety.

BACKGROUND OF THE INVENTION

The invention relates to a covering for objects, in particular in public facilities and/or means of transportation, for preventing the transmission of infections, having a covering material, in particular with a virucidal and/or virostatic and/or bactericidal and/or bacteriostatic and/or fungicidal and/or fungistatic effect, the covering material being intended to be applied externally to surfaces of objects.

The transmission of diseases often takes place by infection in the public domain. Infections may occur as the result of contact with different persons. In the case of an infection, pathogens actively or passively enter the organism and often multiply there. The reaction of the organism that generally follows as a result may manifest itself as an infectious disease. The most common types of infection are viral or fungal infections and bacterial infections. Infections of the aforementioned kind may occur in particular in public facilities or means of transportation, since many people frequent these places.

To reduce the risk of contact infection, it is known from DE 103 05 142 A1 to provide surfaces that have a germicidal effect for the purpose of interrupting the transmission of infections, metals being used for killing the germs. In this case, a metal-doped, dimensionally stable plastic grip is proposed for a door handle and is pushed onto the door handle. Provided on the inside in the front region of the grip is a nipple, which in the pushed-on position engages in a hole drilled in the door handle. The interlocking connection is intended to prevent easy removal of the grip. If the grip is intended to be exchanged or taken off, this is performed by drilling out the nipple. For this purpose, a depression is provided on the outer side of the grip in the region of the nipple, in order to be able to put a drill in place.

The known metal-doped door grip has a tubular form and can be pushed onto correspondingly formed tubular door handles. It is disadvantageous that many door handles have a form that deviates from the form of a tube. Moreover, in the prior art, the door handle and the metal-doped grip represent a unit, since interlocking engagement of the door grip on the door handle is necessary. So far, use of the known door handle with a door grip has not been adopted in practice. The reason for this is likely to be, in particular, that it would be necessary to replace existing door handles, which usually have a form that deviates from the form of a tube and moreover do not have an engaging opening for the interlocking engagement of the door grip.

Also known from practice are fibrous and textile sheet-like materials that comprise ionic copper. These materials are used for example as an inner liner in handbags. The aforementioned fabrics are not suitable for use as a covering because they quickly become soiled, cannot be easily cleaned and, on account of their woven structure, offer the possibility of pathogens firmly attaching themselves there in such an amount that, even with a good virucidal or bactericidal effect, not all the pathogens can be deactivated or killed.

BRIEF SUMMARY OF THE INVENTION

The object of the present invention is thus to provide a covering of the type mentioned at the beginning which can be used for objects of a wide variety of forms, in particular in public facilities and means of transportation, such as door handles, holding rails, grips and the like.

To achieve the aforementioned object, it is mainly provided according to the invention in the case of a covering of the type mentioned at the beginning that the covering material is flexible and can be adapted to the external form of the object. By contrast with the prior art, the covering material is not dimensionally stable but flexible, and can consequently be adapted to the external form of the object. The covering according to the invention is consequently not confined to a specific cross-sectional form of the object to be covered, but can in principle be pulled onto any object of a given diameter, irrespective of the cross-sectional form of the object. Consequently, the application area of the covering according to the invention is increased considerably in comparison with the known covering.

The covering material is preferably produced from a sheet material. On account of the small layer thickness, sheet materials can usually ensure the necessary flexibility of the covering, and consequently the adaptation to the external form of the object. At the same time, the sheet material may be formed with one or more layers. In any case, the sheet material should have at least one layer containing plastic, which then preferably serves as a supporting layer, or at least has a supporting function. Such a sheet not only can be produced in a particularly easy way by extrusion, coextrusion or blown film extrusion, but is also distinguished in particular by very small surface roughness. The surface roughness is preferably less than 10% of the layer thickness of the sheet material, preferably less than 5% and in particular less than 1%. Thus, for example in the case of a sheet with a layer thickness of 300 $\mu$m, a roughness of at most 30 $\mu$m is obtained. The roughness is preferably less than 3 $\mu$m. Ultimately, the small roughness has the effect that pathogens cannot attach themselves sufficiently to the surface, while any attached pathogens are deactivated or killed by the effect of the covering mentioned at the beginning. Moreover, the surface can be easily cleaned. Finally, coverings produced from sheet material have the major advantage that they are extremely inexpensive, since the aforementioned production processes, which incidentally also include casting and calendering, make it possible for large amounts of covering material to be produced at lower cost.

The layer thickness of the sheet material should be between 10 $\mu$m and 10 mm, preferably between 20 $\mu$m and 2000 $\mu$m, more preferably between 50 $\mu$m and 1000 $\mu$m and in particular between 100 and 500 $\mu$m. One effect of such layer thicknesses is that they provide a sufficiently flexible covering material, which can moreover be easily processed and is inexpensive.

Otherwise, as already mentioned, the sheet material should have at least one layer as a supporting layer. This may consist of polyolefins, in particular PE or PP, polyester, polyamide, polyurethane, polyether ester, acrylates, PS, polylactic acid, renewable raw materials, such as cellulose, or biodegradable plastics, such as for example PRA. Moreover, this layer may also contain pigments and further additives, such as for example UV stabilizers, antioxidants, flame retardants or the like.

It is of particular advantage moreover that the covering is either formed as a flexible tube and can be pulled onto the object or else, as an alternative to this, that the covering is in the form of a band and can be wound around the object. Sheet-material tubes or webs of the aforementioned kind can on the one hand be produced relatively easily and inexpensively by the aforementioned processes. On the other hand, tubes and bands can be applied very easily to an object. At the same time, in particular in the case of bands, there is the major advantage that coverings comprising bands do not require that objects are freely accessible at least at one end. Bands can be applied to any objects and to any surfaces, even if the objects do not have free ends, such as for example holding rails, grips or the like that are restrained or secured at both ends. Moreover, in the case of bands, depending on the way in which the band and the object concerned are formed, it is not required for the band to be wound spirally around the object. Winding in the longitudinal direction of the object is also readily possible.

Moreover, it should be pointed out that a covering in the form of a band is understood as comprising band widths greater than 5 mm. Bands in the sense of the present invention are also understood as meaning other layers of sheet material that have, for example, a square or rectangular form with surface areas greater than 1 sqm.

It is of particular advantage in this connection that the plastics material of the covering is formed in such a way that it can be shrunk by the action of heat. Therefore, in this case the plastic layer concerned represents a shrink film. The shrinking, which can be performed in an easy way, allows the covering to be secured on the object quickly and surely, without special means or connecting elements having to be present on the object.

Moreover, adhesive bonding may be used for connecting the covering to the object. For this purpose, the covering may be accompanied, for example in the form of a set, by an adhesive, which is applied to the object before the covering is applied. In particular in the case of a covering in the form of a band, it is appropriate if the covering material has an adhesive coating on its underside, facing the object. The adhesive coating may preferably be a re-releasable adhesive, so that, specifically when there is a misalignment during application, subsequent alignment is easily possible. In this connection, an outer protective layer that is pulled off before application should be provided to protect the adhesive layer. The protective layer may, for example, be siliconized.

It is of particular advantage, moreover, that the covering material is elastically stretchable. The elastic stretchability makes it possible to provide a single type of covering for objects of different diameters that can be applied to objects of different sizes on account of its elasticity. Moreover, as a result of the flexibility and adaptability of the covering material, and in particular as a result of the elastic stretchability, it can be ensured that the covering comes to lie against the surface of the object over its full surface area, or at least substantially over its full surface area, in the state in which it is applied to the object.

In order to make the handling of the covering according to the invention as easy as possible for a wide variety of objects, the covering or the covering material should be wound up and stored with a length of over 1 m, in particular over 3 m, on a roll or the like. The necessary length of covering material for the respective need can then be removed or detached from the roll and applied to the object. The width of the roll is in this case made to match the width of the covering or covering material. Accordingly, the width of the roll should be greater than 5 mm. Rolls with a width of up to 2 m are also possible in principle. Ultimately, the width of the roll, and consequently the width of the covering, determines the intended use, or the size and form of the object to be protected.

To prevent the transmission of infections, the covering material comprises metals that have corresponding properties. Coming into consideration in particular in this respect are copper and especially also silver. The aforementioned metals are distinguished by their virucidal, bactericidal and fungicidal effect.

Particularly good active effects are obtained in the case of copper if this metal is in the ionic form. The use of copper in the form of salts and/or oxides thus comes into consideration especially. On the other hand, in the case of silver, it should be in its elemental form. This produces the best active effects.

The metal should preferably be in the covering material in a particulate form, in particular in the form of nanoparticles, and/or in the form of threads, for example in the form of individual threads or in a lattice-like formation and/or in the form of filaments. The particle size should in this case be between 10 and 2000 nm, preferably between 100 and 1000 nm and more preferably between 200 and 300 nm.

The proportion of the metallic active substance should be between 0.001 and 20% by weight with respect to the total weight of the covering. The proportion preferably lies between 0.01 and 5% by weight and more preferably between 0.1 and 2% by weight.

In particular when a sheet material is used, it is appropriate that the covering material has, at least on its outer side facing away from the object, which in the state of use of the covering represents the gripping side for users, a coating or active layer containing the metal. In this case, a carrier layer that serves substantially for attaching and securing the covering on the respective object is then provided. The coating containing the active substance or the metal is then applied as an active layer to the carrier layer, preferably with a smaller layer thickness than the carrier layer. The ratio of the layer thickness of the carrier layer to the active layer is preferably between 1:1 and 10:1. The particular advantage of the aforementioned coating is that the proportion of metal in the outer active layer can be comparatively great, so that the covering is extremely effective.

Irrespective of whether or not an outer active layer is provided, the metal should in any case be uniformly distributed either in the plastic layer—in the absence of an outer active layer—or else in the outer active layer. The uniform distribution ensures that, even when the outer surface becomes worn, there is always sufficient active material present when an object protected by a covering continues to be grasped.

Moreover, the present invention also relates to a method for applying a covering for preventing the transmission of infections to the surface of an object, in particular in public facilities and/or means of transportation, the covering material of the covering adapting itself flexibly to the external form of the object when it is applied to the object.

Of particular advantage in connection with the method according to the invention is that the covering can be applied to the surface of the object in the fitted state of the object and/or retrospectively, to be precise irrespective of whether the object is secured at one or two ends. In particular, the method according to the invention makes it possible to retrofit already existing objects with a covering for preventing the transmission of infections.

It may be expressly pointed out that the foregoing and also following statements of ranges comprise all interim intervals and individual values, and these are regarded as essential to the invention even if the interim intervals and individual values are not specifically mentioned.

Exemplary embodiments of the invention are described in more detail below on the basis of the drawing. In it, all the features described and/or graphically represented form the subject matter of the present invention on their own or in any desired combination, irrespective of how they are combined in the claims or the way in which the claims refer back.

BRIEF DESCRIPTION OF THE DRAWINGS

FIG. 8 shows a representation of a flexible tube for producing a covering, FIG. 9 shows a representation of a band for producing a covering, FIG. 10 shows a representation of a band stored on a roll for producing coverings.

DETAILED DESCRIPTION OF THE INVENTION

Figure 1:
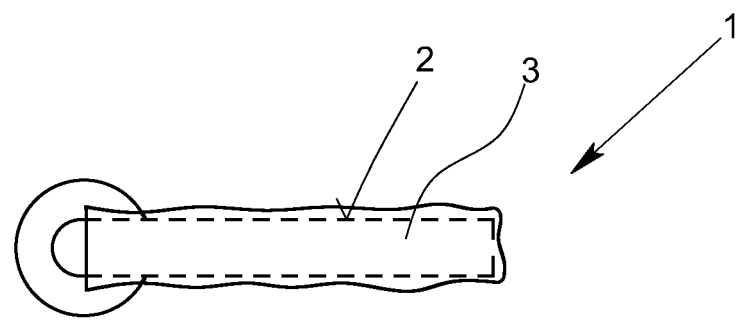
FIG. 1 shows a schematic representation of a covering according to the invention applied to a door handle, in the non-secured state.

In FIGS. 1 to 7, various exemplary embodiments of coverings 1 according to the invention are represented with different objects. In the case of all the embodiments, it is the case that the respective covering 1 is provided for preventing the transmission of infections, and consequently ultimately for providing a sterile surface. For this purpose, the covering 1 has a covering material, which is provided in particular with a virucidal and/or virostatic and/or bactericidal and/or bacteriostatic and/or fungicidal and/or fungistatic effect. In the present case, this is based on the action of corresponding metals that are incorporated in the covering material. In the case of the exemplary embodiments, the metal is silver in its elemental form.

In the present case, the covering material, and consequently the covering 1, is intended for external application to surfaces 2 of objects. The objects may, in principle, be objects of any kind that are handled and/or grasped. In particular, they are objects in the public domain, as in public facilities or public means of transportation. However, the invention is not restricted thereto. In particular, the objects may also be items of equipment in the military sector and/or for ABC protection. This may comprise, for example, weapons and other objects that can be grasped by different people.

In FIGS. 1 to 7, a door handle 3 (FIGS. 1 and 2), a holding rail 4 (FIGS. 3 to 5) and a drinking bottle 5 (FIGS. 6 and 7) are represented by way of example as objects.

In the case of all the embodiments, it is the case that the covering material, and consequently the covering 1, is flexibly formed and adapts itself to the geometry of the body concerned.

Figure 2:
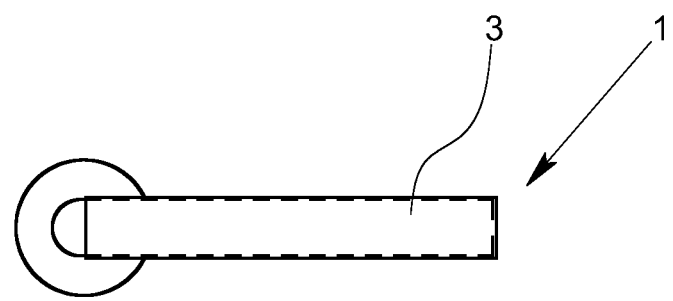
FIG. 2 shows a representation corresponding to FIG. 1 with the covering secured.

In FIGS. 1 to 7, various embodiments of coverings 1 for different objects are thus represented. In the case of the embodiment according to FIGS. 1 and 2, a covering 1 in the form of a flexible tube has been pulled onto a door handle 3, which has a cylindrical form in the present case but is not restricted thereto. In the present case, the flexible tube is closed at the end, which however does not necessarily have to be the case. As the representation according to FIG. 1 reveals, the cross-sectional area of the covering 1 is greater than the cross-sectional area of the door handle 1, so that pulling over is readily possible. The covering 1, formed as a flexible tube, consists in the present case of a shrink film of corresponding plastic, which contracts or shrinks under the influence of heat. In FIG. 2, the shrunk-on state of the covering 1 is represented. In this state, the covering 1 lies against the surface 2 of the door handle 3 over its full surface area.

Figure 3:
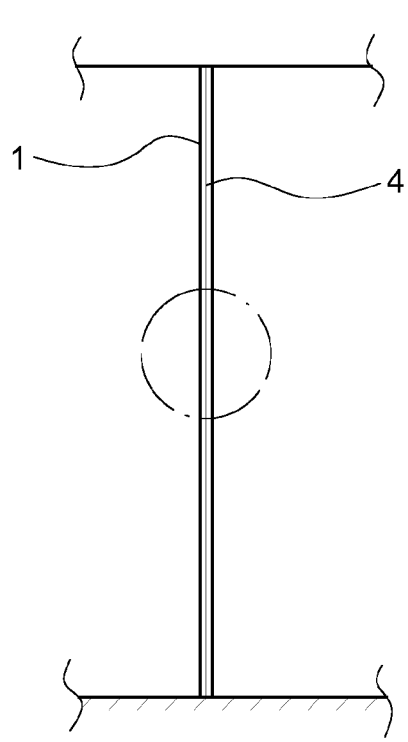
FIG. 3 shows a schematic representation of a covering applied to a holding rail.
Figure 4:
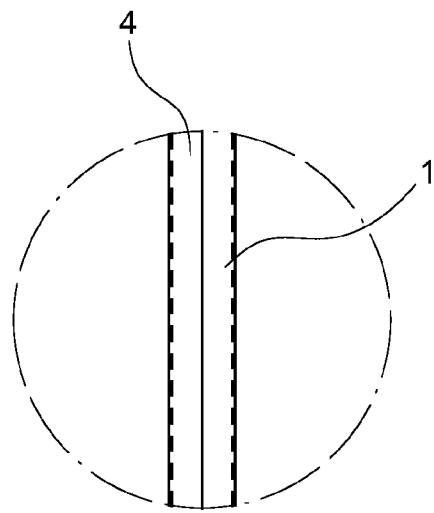
FIG. 4 shows an enlarged representation of a detail of the embodiment according to FIG. 3.

FIG. 3 shows an embodiment in which a holding rail 4 that is respectively secured at its upper and lower ends is provided as the object. Here, too, a covering 1 has been applied to the surface 2 of the holding rail 4. As the representation of a detail according to FIG. 4 reveals, the covering 1 formed as a band has been applied lengthwise to the holding rail 4.

Figure 5:
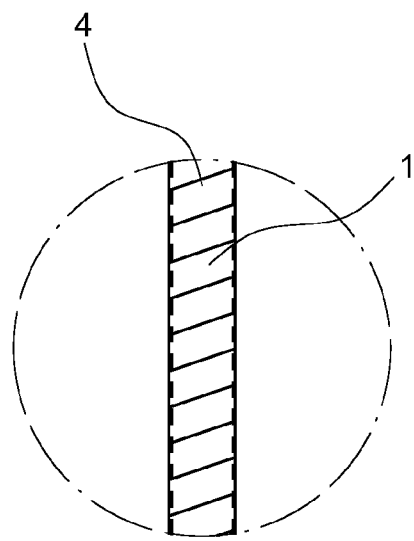
FIG. 5 shows another embodiment corresponding to the representation of the detail in FIG. 4.

An alternative embodiment, in which the covering material is wound spirally around the holding rail 4, is represented in FIG. 5.

The securing of the respective covering 1 may thereby be performed by various measures. In the case of the embodiment represented in FIG. 4, the covering material in the form of a band has an adhesive coating on its underside. Alternatively, it is also possible to apply to the surface 2 of the holding rail 4 adhesive that subsequently serves for providing the connection to the covering 1. In the case of the embodiment represented in FIG. 5, the covering material is elastically stretchable, so that the covering 1 is held on the holding rail 4—ultimately by frictional engagement—and at least substantially without adhesive.

Figures 6, 7:
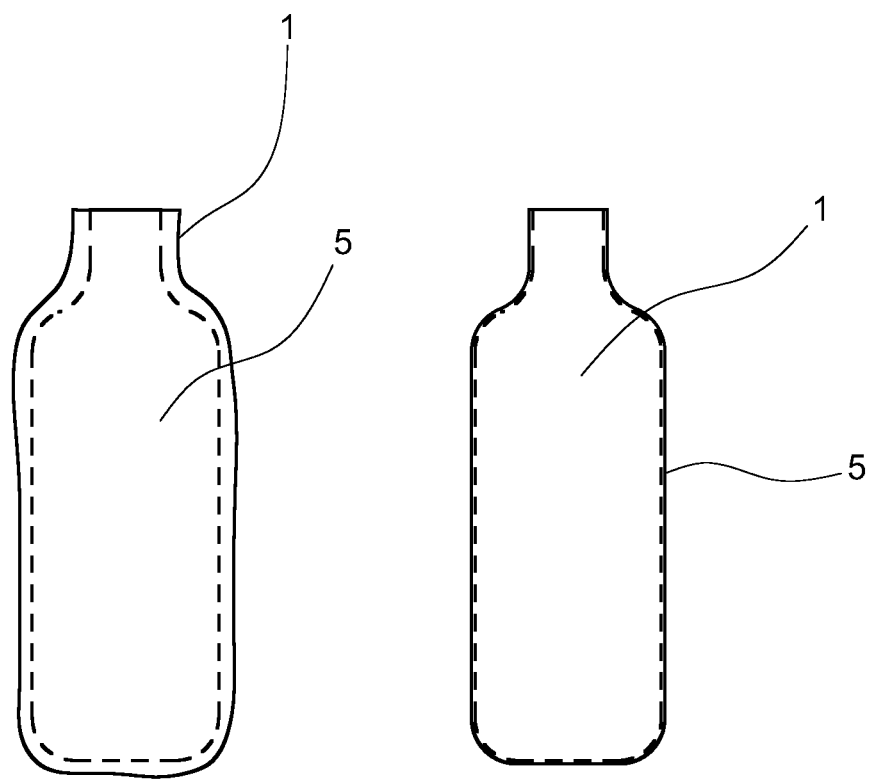
FIG. 6 shows a representation of a drinking bottle with a non-secured covering.
FIG. 7 shows a representation of the drinking bottle from FIG. 6 with the covering secured.

An embodiment in which a drinking bottle 5 is provided as the object is represented in FIGS. 6 and 7. In the case of the embodiment according to FIG. 6, the covering 1 has been pulled loosely over the drinking bottle 5. After shrinking of the covering 1 formed as a shrink film, it lies against the surface 1 of the drinking bottle 5 over its full surface area.

It should be pointed out that, in particular in the case of the embodiment according to FIGS. 6 and 7, in principle a covering 1 of an elastically stretchable covering material may also be used, the covering 1 first being stretched somewhat and then pulled over the object concerned. The covering material subsequently contracts again and the covering 1 lies against the surface 2 of the respective object at least over part of its surface area.

In FIG. 8, a flexible tube 6 for forming one or more coverings 1 is represented. The flexible tube 6 is in the present case a sheet material that can shrink under the effect of heat. In principle, the flexible tube 6 may also be an elastically stretchable material. The dimensions of the flexible tube 6 depend on the respective application, that is to say on the length and diameter of the respective object. The width of the flexible tube 6 in the folded-together state corresponding to FIG. 8 and the cross-sectional area thereof are variable. Thus, flexible tubes with a width from 0.5 cm are possible.

FIG. 9 shows a band 7 for producing one or more coverings 1. In terms of the dimensions, the band 7 corresponds to the aforementioned flexible tube 6. Both the flexible tube 6 and the band 7 ultimately have an endless length.

In FIG. 10, a roll 8 with an endless band 7 for producing coverings 1 is represented. In this case, the band 7 is wound up on itself on the roll 8.

In FIGS. 11 to 14, various layer structures of the covering material for coverings 1 according to the invention are represented. In the case of all the embodiments, the layer thickness of the respective material lies between 100 and 2000 µm. Moreover, in the case of all the embodiments, a supporting layer 9 of plastic is provided.

Figure 11:
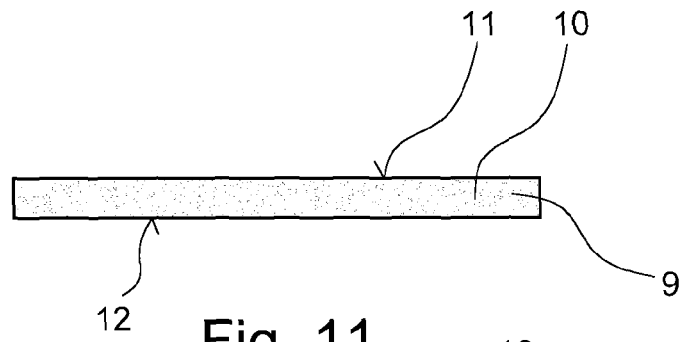
FIG. 11 shows a cross-sectional view of an embodiment of a layer structure of the covering material according to the invention.

In the case of the embodiment according to FIG. 11, there are silver particles 10 in the form of nanoparticles, with a particle size of between 200 and 300 nm, in the supporting layer 9 as the active substance. In the present case, the particles 10 are in the elemental form. Moreover, in the present case, the particles are uniformly distributed over the thickness of the layer. In principle, however, it is also possible for the particles 10 to be provided more at the upper side 11 and less to not at all at the underside 12. The upper side 11 is ultimately the outer active area of the covering 1, facing the user, while the underside 12 is facing the surface 2 of the object in the pulled-on state.

Figure 12:
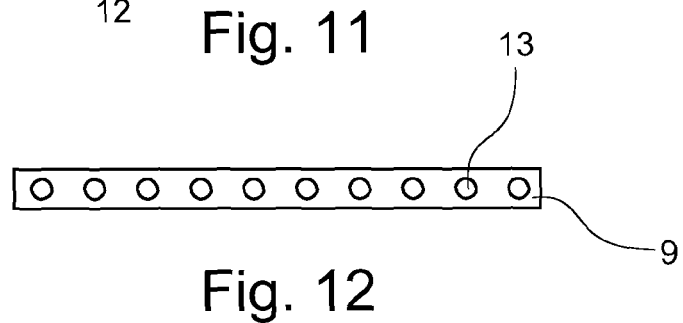
FIG. 12 shows a representation of a further embodiment of a layer structure of the covering material according to the invention.

In the case of the embodiment according to FIG. 12, a multiplicity of threads 13 of the active metal are provided in the supporting layer 9. It is not shown that the arrangement of the threads 13 is ultimately a lattice arrangement. However, a multiplicity of short threads or filaments of the metal may also be provided in the supporting layer 9 without alignment. In the case of the embodiment represented in FIG. 12, the diameter of the threads 13 corresponds approximately to the layer thickness of the supporting layer 9. This does not have to be the case, however. The threads 13 may in principle have a very much smaller diameter. Thus, the diameter of the threads may be less than the layer thickness of the supporting layer 9 by a factor of 1 to 100. Moreover, in the case of the embodiment according to FIG. 12, it is possible for the threads to be provided only in the upper region, that is to say in the region of the upper side 11, and only sporadically or not at all in the region of the underside 12.

Figure 13:
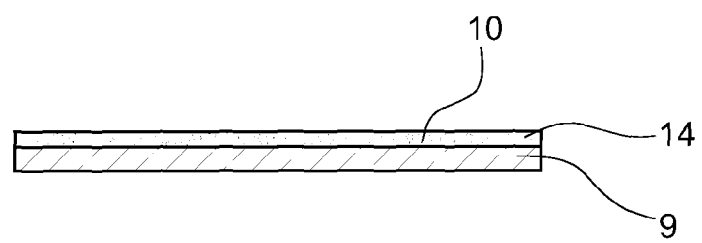
FIG. 13 shows a representation of a further embodiment of a layer structure of the covering material according to the invention and FIG. 14 shows a representation of a further embodiment of a layer structure of the covering material according to the invention.

In the case of the embodiment according to FIG. 13, on the supporting layer 9 there is an active layer 14 with the active metal. The active layer 14 may be formed like one of the layers 11, 12. The thickness of the active layer is preferably less than the thickness of the supporting layer, in particular by a factor of 1 to 50.

Figure 14:
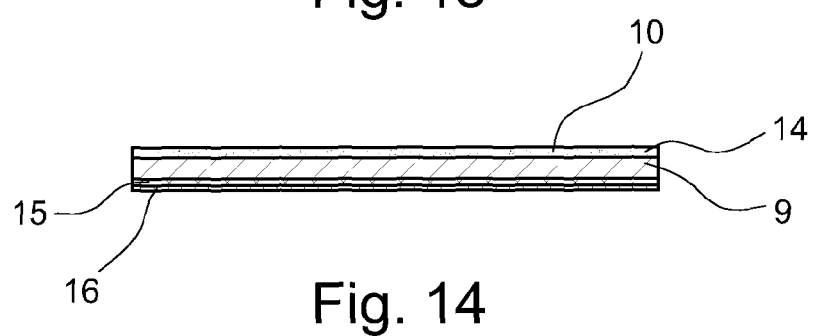

In the case of the embodiment represented in FIG. 14, an adhesive layer 15 and a protective layer 16 have been applied to the underside of a sheet material in a way corresponding to FIG. 13. The protective layer 16 is siliconized and may be pulled off before application of the covering. The adhesive of the adhesive layer 15 may be any known adhesive. A re-releasable adhesive is preferred.

LIST OF DESIGNATIONS

1 Covering
2 Surface
3 Door handle
4 Holding rail
5 Drinking bottle
6 Flexible tube
7 Band
8 Roll
9 Supporting layer
10 Particle
11 Upper side
12 Underside
13 Thread
14 Active layer
15 Adhesive layer
16 Protective layer

The invention claimed is:

1. A covering intended for being applied to the surfaces of objects in public facilities and/or public means of transportation, the covering being capable of preventing the transmission of infections and the covering comprising a covering material having an active substance with a virucidal and/or virostatic and/or bactericidal and/or bacteriostatic and/or fungicidal and/or fungistatic effect, the covering material being intended to be applied externally to surfaces of the objects, the covering material being flexible and able to be adapted to the external form of the object and being produced from a single-layered or multi-layered sheet-like material having at least one layer containing a plastics material, and the active substance being incorporated in the outer layer of the covering material, which outer layer in the state of use of the covering represents the gripping side for users,
    wherein the covering is in the form of a band and can be wound around the objects,
    wherein the covering material is elastically stretchable, and
    wherein the covering material comprises a plastics material shrinkable by the action of heat and formed as a shrink film and wherein the covering material is intended for being shrunk onto the objects.

2. The covering as claimed in claim 1, wherein the covering material has, on its underside facing the objects, an adhesive layer, wherein a protective layer is provided on the adhesive layer.

3. The covering as claimed in claim 2, wherein the adhesive layer comprises a re-releasable adhesive and wherein the protective layer comprises a siliconized layer.

4. The covering as claimed in claim 1, wherein the covering material is wound up and stored on a roll.

5. The covering as claimed in claim 1, wherein the covering material comprises at least one metal as the active substance.

6. The covering as claimed in claim 5, wherein the metal comprises at least one of copper and silver.

7. The covering as claimed in claim 1, wherein the covering material has, at least on its side facing away from the objects, an active layer containing the metal.

8. A method for applying a covering comprising a flexible covering material to the surface of an object in public facilities and/or in public means of transportation, for the purpose of preventing the transmission of infections,
    wherein the method comprises the use of a covering comprising a covering material having an active substance with a virucidal and/or virostatic and/or bactericidal and/or bacteriostatic and/or fungicidal and/or fungistatic effect, the covering material being intended to be applied externally to the surfaces of the object, the covering material being flexible and able to be adapted to the external form of the object and being produced from a single-layered or multi-layered sheet-like material having at least one layer containing a plastics material, and the active substance being incorporated in the outer layer of the covering material, which outer layer in the state of use of the covering represents the gripping side for users, wherein the covering is in the form of a band and is wound around the object and wherein the covering material comprises a plastics material shrinkable by the action of heat and formed as a shrink film, and wherein the covering material is shrunk onto the object to secure the covering material to the object.

* * * * *